US010765888B2

(12) United States Patent
Sjolund et al.

(10) Patent No.: US 10,765,888 B2
(45) Date of Patent: *Sep. 8, 2020

(54) SYSTEM AND METHOD FOR AUTOMATIC TREATMENT PLANNING

(71) Applicants: Elekta, Inc., Atlanta, GA (US); Elekta AB, Stockholm (SE)

(72) Inventors: Jens Olof Sjolund, Stockholm (SE); Xiao Han, Chesterfield, MO (US)

(73) Assignees: Elekta AB, Stockholm (SE); Elekta, Inc., Atlanta, GA (US)

( * ) Notice: Subject to any disclaimer, the term of this patent is extended or adjusted under 35 U.S.C. 154(b) by 202 days.

This patent is subject to a terminal disclaimer.

(21) Appl. No.: 16/029,147

(22) Filed: Jul. 6, 2018

(65) Prior Publication Data
US 2018/0311510 A1 Nov. 1, 2018

Related U.S. Application Data

(63) Continuation of application No. 14/308,450, filed on Jun. 18, 2014, now Pat. No. 10,046,177.

(51) Int. Cl.
*A61N 5/10* (2006.01)
*G06N 99/00* (2019.01)
(Continued)

(52) U.S. Cl.
CPC ............ *A61N 5/1038* (2013.01); *A61B 6/032* (2013.01); *A61N 5/103* (2013.01); *A61N 5/1039* (2013.01);
(Continued)

(58) Field of Classification Search
CPC .... A61N 5/103; A61N 5/1038; A61N 5/1039; A61N 2005/1041; G06N 5/04; G06N 7/005; G06N 20/00; A61B 6/032
See application file for complete search history.

(56) References Cited

U.S. PATENT DOCUMENTS

| 6,430,307 B1 | 8/2002 | Souma et al. |
| 7,362,848 B2 | 4/2008 | Saracen et al. |

(Continued)

FOREIGN PATENT DOCUMENTS

| AU | 2015275750 A1 | 12/2016 |
| CN | 101267858 A | 9/2008 |

(Continued)

OTHER PUBLICATIONS

"Australian Application Serial No. 2015275750, Response Filed Mar. 19, 2019to Second Examination Report dated Mar. 8, 2019", w/o English Claims, 3 pgs.

(Continued)

*Primary Examiner* — Christine H Matthews
*Assistant Examiner* — Joshua Daryl D Lannu
(74) *Attorney, Agent, or Firm* — Schwegman Lundberg & Woessner, P.A.; Sanjay Agrawal

(57) ABSTRACT

The present disclosure relates to systems, methods, and computer-readable storage media for radiotherapy. Embodiments of the present disclosure may receive a plurality of training data and determine one or more predictive models based on the training data. The one or more predictive models may be determined based on at least one of a conditional probability density associated with a selected output characteristic given one or more selected input variables or a joint probability density. Embodiments of the present disclosure may also receive patient specific testing data. In addition, embodiments of the present disclosure may predict a probability density associated with a characteristic output based on the one or more predictive models and the patient specific testing data. Moreover, embodiments of the present disclosure may generate a new treatment plan based on the prediction and may use the new treatment plan to validate a previous treatment plan.

22 Claims, 8 Drawing Sheets

(51) Int. Cl.
*G06N 7/00* (2006.01)
*G06N 5/04* (2006.01)
*A61B 6/03* (2006.01)
*G06N 20/00* (2019.01)

(52) U.S. Cl.
CPC .............. *G06N 5/04* (2013.01); *G06N 7/005* (2013.01); *G06N 20/00* (2019.01); *A61N 2005/1041* (2013.01)

(56) References Cited

U.S. PATENT DOCUMENTS

| | | | |
|---|---|---|---|
| 7,593,505 | B2 | 9/2009 | Saracen et al. |
| 8,121,252 | B2 | 2/2012 | Nord et al. |
| 8,363,785 | B2 | 1/2013 | Nord et al. |
| 8,688,618 | B2 | 4/2014 | Mcnutt et al. |
| 10,046,177 | B2 | 8/2018 | Sjölund et al. |
| 2004/0015070 | A1 | 1/2004 | Liang et al. |
| 2004/0146141 | A1* | 7/2004 | Svatos ................... A61N 5/103 378/65 |
| 2008/0008291 | A1 | 1/2008 | Alakuijala et al. |
| 2009/0234627 | A1 | 9/2009 | Yu et al. |
| 2009/0234628 | A1 | 9/2009 | Yu et al. |
| 2010/0057651 | A1* | 3/2010 | Fung ...................... G06N 7/005 706/12 |
| 2011/0153547 | A1 | 6/2011 | Mcnutt et al. |
| 2011/0289036 | A1 | 11/2011 | Stojadinovic et al. |
| 2012/0014507 | A1 | 1/2012 | Wu et al. |
| 2012/0280135 | A1 | 11/2012 | Bal et al. |
| 2012/0310615 | A1 | 12/2012 | Moore et al. |
| 2013/0077752 | A1 | 3/2013 | Zankowski et al. |
| 2013/0085343 | A1 | 4/2013 | Toimela et al. |
| 2015/0367145 | A1 | 12/2015 | Sjolund et al. |

FOREIGN PATENT DOCUMENTS

| | | |
|---|---|---|
| CN | 102365111 A | 2/2012 |
| CN | 103282967 A | 9/2013 |
| EP | 3157627 A1 | 4/2017 |
| JP | 2007509644 A | 4/2007 |
| RU | 2012118760 A | 11/2013 |
| RU | 2017101161 A | 7/2018 |
| WO | WO-2011073820 A1 | 6/2011 |
| WO | WO-2012085722 A1 | 6/2012 |
| WO | WO-2015042727 A1 | 4/2015 |
| WO | WO-2015193776 A1 | 12/2015 |

OTHER PUBLICATIONS

"Australian Application Serial No. 2015275750, Second Examination Report dated Mar. 8, 2019", 5 pgs.
"Russian Application Serial No. 2017101161, Response Filed Dec. 26, 2018 to Office Action dated Oct. 26, 2018", w/English Claims, 115 pgs.
"Chinese Application Serial No. 201580032255.9, Office Action dated Sep. 17, 2019", w/ English translation, 13 pgs.
"Japanese Application Serial No. 2016-574096, Response filed Oct. 23, 2019to Office Action dated Jul. 30, 2019", w/ English Claims, 10 pgs.
"U.S. Appl. No. 14/308,450, Advisory Action dated Nov. 1, 2017", 3 pgs.
"U.S. Appl. No. 14/308,450, Examiner Interview Summary dated May 11, 2017", 3 pgs.
"U.S. Appl. No. 14/308,450, Final Office Action dated Aug. 10, 2017", 17 pgs.
"U.S. Appl. No. 14/308,450, Non Final Office Action dated Jan. 13, 2017", 24 pgs.
"U.S. Appl. No. 14/308,450, Non Final Office Action dated Feb. 3, 2016", 26 pgs.
"U.S. Appl. No. 14/308,450, Notice of Allowance dated May 3, 2018", 8 pgs.

"U.S. Appl. No. 14/308,450, Response filed May 3, 2016 to Non Final Office Action dated Feb. 3, 2016", 19 pgs.
"U.S. Appl. No. 14/308,450, Response filed May 15, 2017 to Non Final Office Action dated Jan. 13, 2017", 18 pgs.
"U.S. Appl. No. 14/308,450, Response filed Sep. 29, 2017 to Final Office Action dated Aug. 10, 2017", 20 pgs.
"U.S. Appl. No. 14/308,450, Response filed Dec. 5, 2017 to Advisory Action dated Nov. 1, 2017", 19 pgs.
"International Application Serial No. PCT/IB2015/054440, International Search Report dated Aug. 21, 2015", 4 pgs.
"International Application Serial No. PCT/IB2015/054440, Written Opinion dated Aug. 21, 2015", 6 pgs.
Binbin, Wu, et al., "Data-Driven Approach to Generating Achievable Dose-Volume Histogram Objectives in Intensity-Modulated Radiotherapy Planning", Int. J. Radiation Oncology Bioi. Phys., vol. 79,No. 4,, (2011), 1241-1247.
Binbin, Wu, "Patient geometry-driven information retrieval for IMRT treatment plan quality control", Med. Phys. 36 (12), (Dec. 2009), 5497-5505.
Kiaofeng, Zhu, et al., "A planning quality evaluation tool for prostate adaptive IMRT based on machine learning", Med. Phys. 38, (Feb. 2011), 719-726.
Lindsey, Appenzoller M., et al., "Predicting dose-volume histograms for organs-at-risk in IMRT planning", Med. Phys. 39, (2012).
Michael, Kazhdan, et al., "A planning quality evaluation tool for prostate adaptive IMRT based on machine learning", [Med. Phys. 38, 719 (2011 )], Med. Phys. 38 (5), (May 2011), 2820 pgs.
Ollivier, Gayou, et al., "EUCLID: An Outcome Analysis Tool for High-Dimensional Clinical Studies", Physics in Medicine and Biology,, (2007), 1705-1719.
Patricio, Simari, et al., "A Statistical Approach for Achievable Dose Querying in IMRT Planning", Med. Image Comput. Comput. Assist. Interv., (2010), 521-528.
Renzhi, Lu, et al., "Learning the Relationship between Patient Geometry and Beam Intensity in Breast Intensity-Modulated Radiotherap", IEEE Trans. Biomed. Eng., (May 2006), 908-920.
Wade, Smith P., et al., "A Decision Aid for Intensity-Modulated Radiation-Therapy Plan Selection in Prostate Cancer Based on a Prognostic Bayesian Network and a Markov Model", Artificial Intelligence in Medicine, (2009), 119-130.
Zarepisheh, M, et al., "A moment-based approach for DVH-guided radiotherapy treatment plan optimization", Phys. Med. Biol. 58, (2013), 1869-1887.
Zinchenko, Y, et al., "Controlling the dose distribution with gEUD-type constraints within the convex radiotherapy optimization framework", Phys. Med. Bioi. 53, (2088), 3231-3250.
"International Application Serial No. PCT/IB2015/054440, International Preliminary Report on Patentability dated Dec. 29, 2016", 8 pgs.
"Russian Application Serial No. 2017101161, Office Action dated Oct. 26, 2018", W/English Translation, 18 pgs.
"Russian Application Serial No. 2017101161, Response filed Aug. 31, 2018 to Office Action dated Mar. 1, 2018", w/English Translation, 42 pgs.
U.S. Appl. No. 14/308,450 U.S. Pat. No. 10,046,177, filed Jun. 18, 2014, System and Method for Automatic Treatment Planning.
"Japanese Application Serial No. 2016-574096, Office Action dated Jul. 30, 2019", w/ English translation, 5 pgs.
"Japanese Application Serial No. 2016-574096, Response filed Jun. 5, 2019to Office Action dated Mar. 19, 2019", w/ English claims, 13 pgs.
"Australian Application Serial No. 2015275750, First Examination Report dated May 23, 2018", 4 pgs.
"Russian Application Serial No. 2017101161, Office Action dated Mar. 1, 2018", w/English Translation, 9 pgs.
"Japanese Application Serial No. 2016-574096, Office Action dated Mar. 19, 2019", w/ English translation, 9 pgs.
"Chinese Application Serial No. 201580032255.9, Office Action dated Apr. 9, 2020", w/English Translation, 12 pgs.
"Chinese Application Serial No. 201580032255.9, Response filed Feb. 3, 2020 to Office Action dated Sep. 17, 2019", w/ English claims, 19 pgs.

(56) References Cited

OTHER PUBLICATIONS

"European Application Serial No. 15731400.6, Communication Pursuant to Article 94(3) EPC dated Mar. 12, 2020", 4 pgs.

* cited by examiner

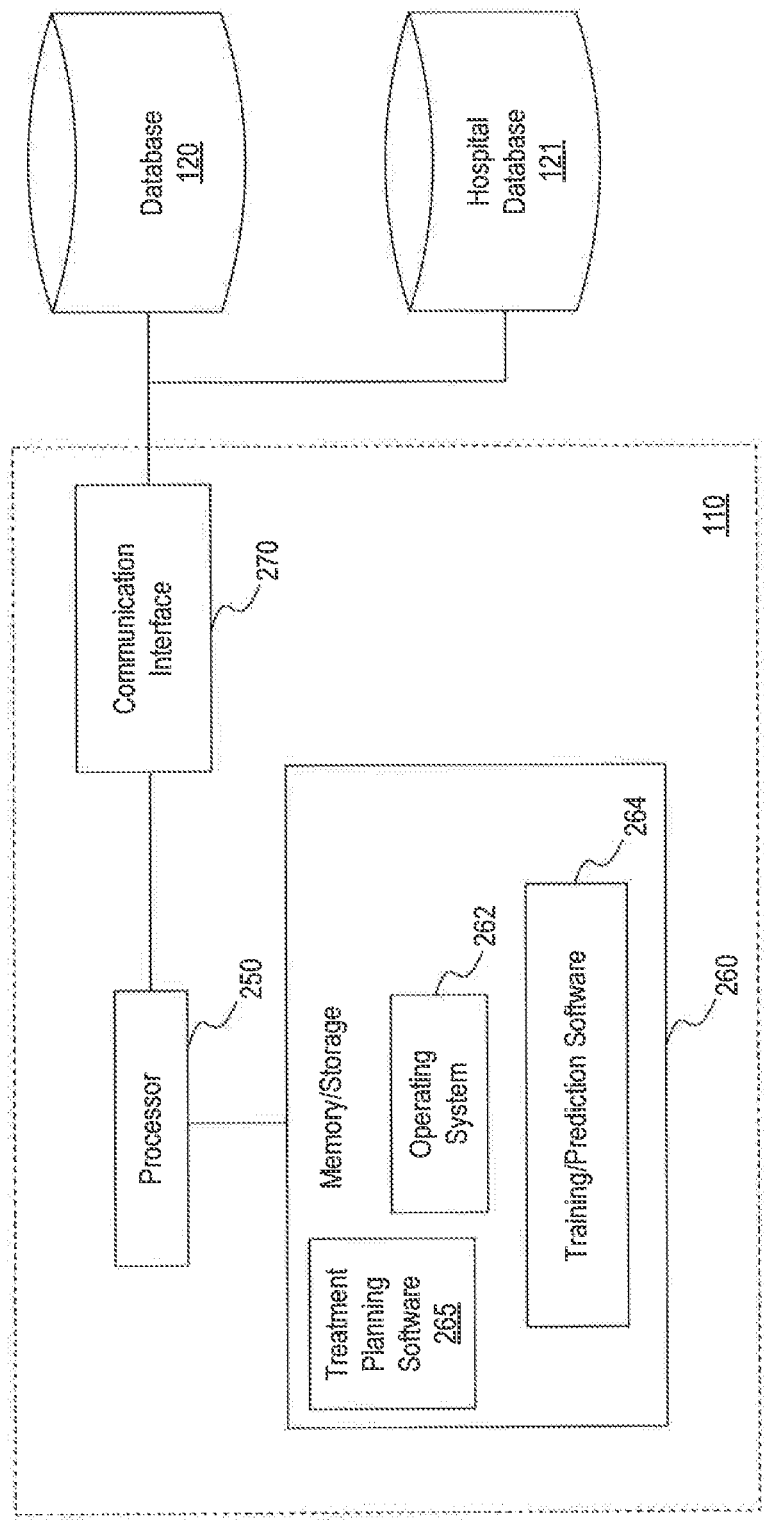

SYSTEM AND METHOD FOR AUTOMATIC TREATMENT PLANNING

PRIORITY APPLICATIONS

This application is a continuation of and claims the benefit of priority to U.S. application Ser. No. 14/308,450, filed Jun. 18, 2014, which is hereby incorporated by reference in its entirety.

TECHNICAL FIELD

This disclosure relates generally to radiation therapy or radiotherapy. More specifically, this disclosure relates to systems and methods for training and/or predicting data for use in developing a radiation therapy treatment plan to be used during radiotherapy.

BACKGROUND

Radiotherapy is used to treat cancers and other ailments in mammalian (e.g., human and animal) tissue. One such radiotherapy technique is a Gamma Knife, by which a patient is irradiated by a large number of low-intensity gamma rays that converge with high intensity and high precision at a target (e.g., a tumor). In another embodiment, radiotherapy is provided using a linear accelerator, whereby a tumor is irradiated by high-energy particles (e.g., electrons, protons, ions and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs).

Traditionally, for each patient, a radiation therapy treatment plan ("treatment plan") may be created using an optimization technique based on clinical and dosimetric objectives and constraints (e.g., the maximum, minimum, and mean doses to the tumor and critical organs). The treatment planning procedure may include using a three-dimensional image of the patient to identify a target region (e.g., the tumor) and to identify critical organs near the tumor. Creation of a treatment plan can be a time consuming process where a planner tries to comply with various treatment objectives or constraints (e.g., dose volume histogram (DVH) objectives), taking into account their individual importance (e.g., weighting) in order to produce a treatment plan which is clinically acceptable. This task can be a time-consuming trial-and-error process that is complicated by the various organs at risk (OARs, because as the number of OARs increases (e.g., up to thirteen for a head-and-neck treatment), so does the complexity of the process. OARs distant from a tumor may be easily spared from radiation, while OARs close to or overlapping a target tumor may be difficult to spare. Segmentation may be performed to identify the OARs and the area to be treated, for example, a planning target volume (PTV). After segmentation, a dose plan may be created for the patient indicating the desirable amount of radiation to be received by the PTV (e.g., target) and/or the OARs. The PTV may have an irregular volume and may be unique as to its size, shape and position. A treatment plan can be calculated after optimizing a large number of plan parameters to ensure that the maximum dose is provided to the PTV while as low a dose as possible is provided to surrounding healthy tissue. Therefore, a radiation therapy treatment plan may be determined by balancing efficient control of the dose to treat the tumor against sparing any OAR. Typically, the quality of a radiation treatment plan may depend upon the level of experience of the planner. Further complications may be caused by anatomical variations between patients.

Currently, most treatment planning procedures limit the parameters considered to those associated with the specific patient or to the specific treatment session. Experience generated from previously developed treatment plans for the same patient, or similar treatment procedures for patients having the same kind of tumor with similar size and location taking into account potential outcomes (e.g., dose applied, success rate, survival time and the like), however, has not been effectively used in the procedures of developing new plans. What is needed is the ability to utilize previous treatment plans to predict objective parameters for one or more outcomes that may be used to generate a radiation therapy treatment plan, which may provide an optimized dose to be delivered to treat the tumor, while minimizing exposure to the one or more OARs.

SUMMARY

Certain embodiments of the present disclosure relate to a radiotherapy system. The radiotherapy system may comprise a memory storing computer executable instructions and a processor device communicatively coupled to the memory. The processor device may be configured to execute the computer executable instructions for receiving a plurality of training data and determining one or more predictive models based on the training data. The one or more predictive models may be determined based on at least one of a conditional probability density associated with a selected output characteristic given one or more selected input variables or a joint probability density. The processor device may also be configured to execute the computer executable instructions for receiving patient specific testing data. In addition, the processor device may be configured to execute the computer executable instructions for predicting a probability density associated with a characteristic output based on the one or more predictive models and the patient specific testing data. Moreover, the processor device may be configured to execute the computer executable instructions for generating a new treatment plan based on the prediction.

Certain embodiments of the present disclosure relate to a method for prediction in a radiotherapy system. The method may be implemented by a processor device executing a plurality of computer executable instructions. The method may comprise receiving a plurality of training data. The training data may include a plurality of training samples. Each of the training samples may comprise a feature vector and an output vector. The method may also comprise determining a joint probability density associated with the feature vector and the corresponding output vector. In addition, the method may comprise generating one or more predictive models based on the joint probability density and storing the one or more predictive models in a memory. The method may also comprise receiving a plurality of patient specific testing data. The patient specific testing data may comprise a plurality of testing samples. The method may also comprise determining a probability density for a feature vector associated with each testing sample of the patient specific testing data. In addition, the method may comprise predicting a probability density for an output vector associated with each testing sample of the patient specific testing data using (1) the probability density for the feature vector associated with the patient specific testing data and (2) the one or more predictive models. Moreover, the method may comprise generating a new treatment plan based on the prediction.

Certain embodiments of the present disclosure relate to a non-transitory computer-readable storage medium having computer-executable instructions stored thereon. The computer-executable instructions, when executed by a processor device, may direct the processor device to receive a plurality of training data. The training data may include a plurality of training samples. Each of the training samples may comprise a feature vector and an output vector. The computer-executable instructions may also direct the processor device to determine a joint probability density associated with the feature vector and the corresponding output vector and determine a conditional probability density associated with the output vector given the feature vector. In addition, the computer-executable instructions may direct the processor device to generate one or more predictive models based on at least one of the joint probability density or the conditional probability density and to store the one or more predictive models in a memory. Moreover, the computer-executable instructions may direct the processor device to receive a plurality of patient specific testing data. The patient specific testing data may comprise a plurality of testing samples. The computer-executable instructions may also direct the processor device to determine a probability density associated for a feature vector associated with each testing sample of the patient specific testing data. In addition, the computer-executable instructions may direct the processor device to predict a probability density of an output vector associated with each testing sample of the patient specific testing data using (1) the probability density for the feature vector associated with the patient specific testing data and (2) the one or more predictive models. Moreover, the computer-executable instructions may direct the processor device to generate a new treatment plan based on the prediction and validate a previous treatment plan based on the new treatment plan.

Additional objects and advantages of the present disclosure will be set forth in part in the following detailed description, and in part will be obvious from the description, or may be learned by practice of the present disclosure. The objects and advantages of the present disclosure will be realized and attained by means of the elements and combinations particularly pointed out in the appended claims.

It is to be understood that the foregoing general description and the following detailed description are exemplary and explanatory only, and are not restrictive of the invention, as claimed.

BRIEF DESCRIPTION OF THE DRAWINGS

The accompanying drawings, which constitute a part of this specification, illustrate several embodiments and, together with the description, serve to explain the disclosed principles.

FIG. 2C illustrates a data processing device and a database used in a radiotherapy system, according to some embodiments of the present disclosure.

DETAILED DESCRIPTION

Figure 1:
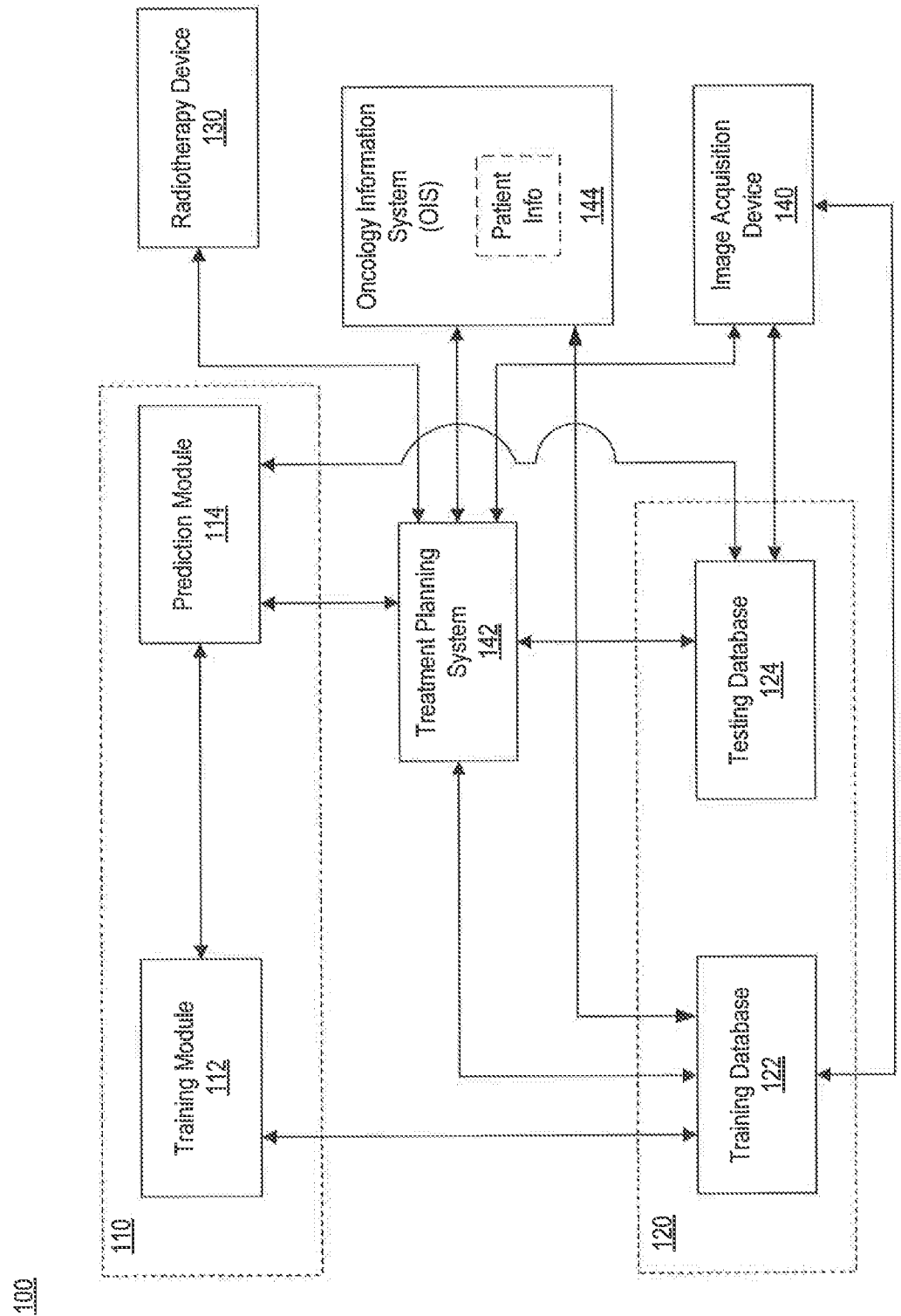
FIG. 1 illustrates an exemplary radiotherapy system, according to some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be interpreted as open ended, in that, an item or items following any one of these words is not meant to be an exhaustive listing of such item or items, or meant to be limited to only the listed item or items. And the singular forms "a," "an," and "the" are intended to include plural references, unless the context clearly dictates otherwise.

Systems and methods consistent with the present disclosure are directed to generating a radiotherapy treatment plan or validating a radiotherapy treatment plan using statistical information derived from past or previous treatment plans. As used herein, a past/previous treatment plan refers to a plan for a radiotherapy treatment of the same patient or a different patient that was conducted any time before the current treatment was generated. For instance, in the case of adaptive radiotherapy, a treatment plan may be initially prepared for a patient, but for each fraction of treatment the plan may be updated; therefore, any plan created prior to the update may be considered as a past/previous treatment plan. The use of the statistical information may improve consistency, accuracy, and efficiency in the treatment planning process because similarities between the new and past plans can be drawn and utilized. For example, patients having the same kind of tumors with similar size and located at similar body part (e.g., prostate, head and neck, lung, brain, and the like) may share similar treatment procedures. Past treatment plans may provide valuable information regarding the link between observations (e.g., kind of tumor, size of tumor, or location of the tumor) and parameters/outcomes in the past treatments (e.g., dose applied, success rate, survival time, and the like).

A training module may use the information of the past treatment plans to derive statistical estimations of various parameters and/or relationships among these parameters. A prediction module may then use the one or more predictive modules to predict one or more objective parameters (e.g., outcomes) that can be used to develop a treatment plan. As used herein, training data may refer to information regarding the past treatment plans; predictive models refer to statistical estimations or derivations drawn or calculated from the past treatment plans; testing data refer to information regarding the new treatment plan; prediction data refer to predictions of parameters or likely outcomes of the new treatment plan.

FIG. 1 illustrates an exemplary radiotherapy system 100, according to some embodiments of the present disclosure. Radiotherapy system 100 may include a training module 112, a prediction module 114, a training database 122, a testing database 124, a radiotherapy device 130, and an image acquisition device 140. Radiotherapy system 100 may also be connected to a treatment planning system (TPS) 142 and an oncology information system (OIS) 144, which may provide patient information. In addition, radiotherapy system 100 may include a display device and a user interface (not shown).

As shown in FIG. 1, training module 112 may communicate with training database 122 to receive training data. The training data stored in training database 122 may be obtained from a treatment planning system 142, which may store data of previous radiotherapy treatment sessions (e.g., treatment planning system 142 may store previously developed treatment plans for a particular patient to be treated and for other patients, as well as other radiotherapy information). For example, treatment planning system 142 may provide information about a particular dose to be applied to a patient and other radiotherapy related information (e.g., type of therapy: such as image guided radiation therapy (IGRT), intensity modulated radiation therapy (IMRT), stereotactic radiotherapy; the number of beams; the beam angles; the dose per beam; and the like). In addition, the training data may also include image data to be obtained from image acquisition device 140. For example, image acquisition device 140 may provide medical images (e.g., Magnetic Resonance Imaging (MRI) images, 3D MRI, 2D streaming MRI, 4D volumetric MRI, Computed Tomography (CT) images, Cone-Beam CT, Positron Emission Tomography (PET) images, functional MRI images (e.g., fMRI, DCE-MRI and diffusion MRI), X-ray images, fluoroscopic image, ultrasound images, radiotherapy portal images, single-photo emission computed tomography (SPECT) images, and the like) of a patient. In some embodiments, the training data may be collected from an Oncology Information System (OIS 144 (e.g., patient information, medical lab results, and the like).

Training module 112 may use the training data received from training database 122 to generate trained data. The trained data may be used to determine a prediction model that may be utilized by the prediction module 114. As described above, prediction model may refer to derivations drawn or calculated from the past treatment plans. In addition, prediction model may include, for example, a conditional probability of an outcome (e.g., a certain dose received by a spatial volume or a voxel) given an observation of a certain property (e.g., a distance between the voxel and the boundary of a target such as a tumor). In another example, prediction model may include a conditional probability of a certain survival time given a tumor size.

Prediction module 114 may receive the one or more prediction models from training module 112 and use the one or more prediction models to predict certain objective parameters, such as properties or outcomes, in order to generate a new treatment plan. For example, prediction module 114 may receive testing data from testing database 124. The testing data may include information such as imaging data (e.g., MRI, CT, X-ray, PET, SPECT, and the like), organ or volume of interest segmentation data, functional organ modeling data (e.g., serial versus parallel organs, and appropriate dose response models), radiation dosage (e.g., also including dose-volume histogram (DVH) information), lab data (e.g., hemoglobin, platelets, cholesterol, triglycerides, creatinine, sodium, glucose, calcium, weight), vital signs (blood pressure, temperature, respiratory rate and the like), genomic data (e.g., genetic profiling), demographics (age, sex, ethnicity), other diseases affecting the patient (e.g., cardiovascular disease, respiratory disease, diabetes, radiation hypersensitivity syndromes, and the like), medications and drug reactions, diet and lifestyle (e.g., smoking or non-smoking), environmental risk factors, tumor characteristics (histological type, tumor grade, hormone and other receptor status, tumor size, vascularity cell type, cancer staging, gleason score), previous treatments (e.g., surgeries, radiation, chemotherapy, hormone therapy), lymph node and distant metastases status, genetic/protein biomarkers (e.g., such as MYC, GADD45A, PPM1D, BBC3, CDKN1A, PLK3, XPC, AKT1, RELA, BCL2L1, PTEN, CDK1, XIAP, and the like), single nucleotide polymorphisms (SNP) analysis (e.g., XRCC1, XRCC3, APEX1, MDM2, TNFR, MTHFR, MTRR, VEGF, TGFβ, TNFα), and the like.

The testing data stored in testing database 124 may further include image data that may be obtained from image acquisition device 140. For example, image acquisition device 140 may provide medical images (e.g., MRI images, CT images, PET images, MRI images, X-ray images, ultrasound images, radiotherapy portal images, single-photo emission computed tomography (SPECT) images, and the like) of the new patient.

The testing data, as described above, and other radiotherapy information stored in testing database 124 may also be obtained from treatment planning system 142 and oncology information system 144. Testing data may be stored in testing database 124 before it is received by prediction module 114.

Alternatively, during adaptive radiotherapy, the testing data may be received by prediction module 114 directly from radiotherapy device 130. In some embodiments, testing data may be retrieved from radiotherapy device 130 in an online mode, e.g., while radiotherapy device 130 is in active operation of performing radiotherapy treatment (e.g., actual dose delivered to a patient). In other embodiments, testing data may be retrieved from radiotherapy device 130 in an offline mode, e.g., while radiotherapy device 130 is not in active operation of performing radiotherapy treatment.

After prediction module 114 generates a plurality of objective parameters based on the testing data and the prediction model, the plurality of objective parameters may be used to develop a treatment plan. The developed treatment plan may be for a patient currently undergoing radiotherapy (e.g., the treatment plan may be updated (adapted) based on current parameters). Alternatively, the developed treatment plan may be for a new patient. The treatment plan may be used by radiotherapy device 130 to perform a treatment in accordance with the treatment plan.

In some embodiments, radiotherapy device 130 may be local with respect to prediction module 114. For example, radiotherapy device 130 and prediction module 114 may be located in the same room of a medical facility/clinic. In other embodiments, radiotherapy device 130 may be remote with respect to prediction module 114 and the data communication between radiotherapy device 130 and prediction module 114 via the treatment planning system 142 may be carried out through a network (e.g., a local area network (LAN); a wireless network; a cloud computing environment such as software as a service, platform as a service, infrastructure as a service; a client-server; a wide area network (WAN); and the like). Similarly, the communication links between training module 112 and training database 122, between training module 112 and prediction module 114, between prediction module 114 and testing database 124, between testing database 124 and treatment planning system 142, between training database 122 and oncology information system 144, between treatment planning system 142 and oncology information system 144, between treatment planning system 142 and radiation therapy device 130, between image acquisition device 140 and testing database 124, between image acquisition device 140 and treatment planning system 142, between image acquisition device and training database 122, may also be implemented in a local or remote manner.

In some embodiments, training module 112 and prediction module 114 may be implemented in a single data processing device 110. For example, training module 112 and prediction module 114 may be implemented as different software programs operating on the same hardware device, as will be described in greater detail later with respect to FIG. 2C. Similarly, training database 122 and testing database 124 may be implemented as a single database 120. For example, a single database may store both the training data and testing data. It is contemplated that any one of training module 112, prediction module 114, training database 122, and testing database 124 may be implemented as a stand-alone module.

Image acquisition device 140 may include an MRI imaging device, a CT imaging device, a PET imaging device, an ultrasound device, a fluoroscopic device, a SPECT imaging device, or other medical imaging devices for obtaining one or more medical images of a patient. Image acquisition device 140 may provide the medical images to treatment planning system 142, testing database 124, and/or training database 122.

Figure 2A:
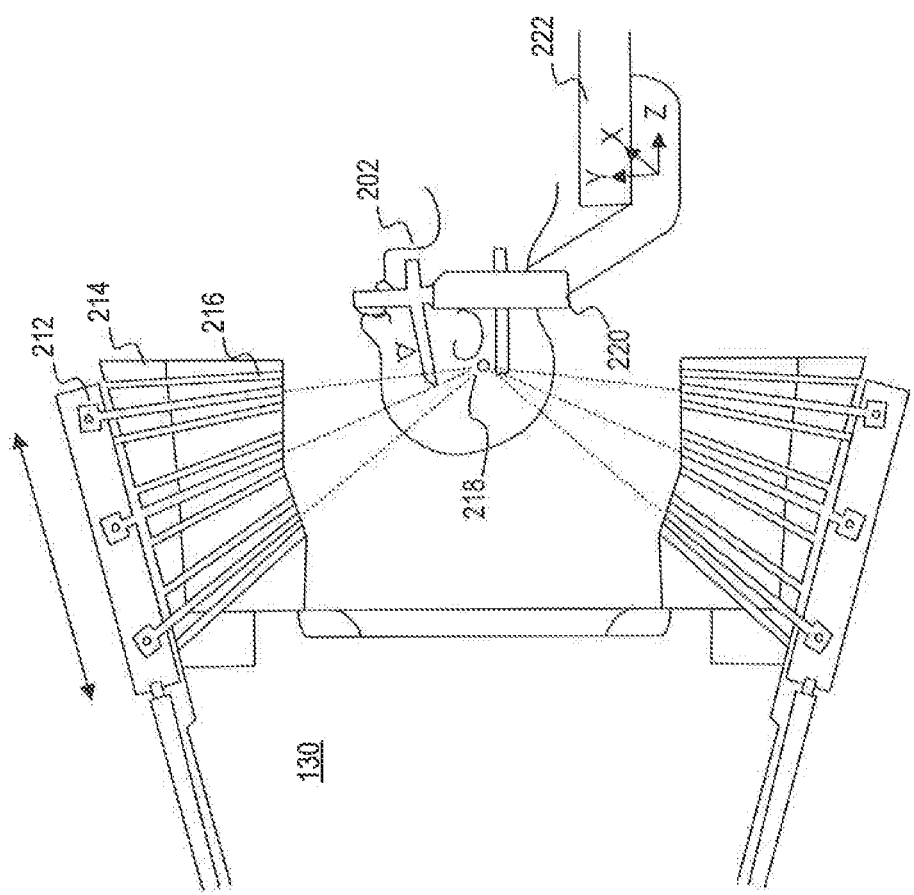
FIG. 2A illustrates a radiotherapy device, a Gamma Knife, according to some embodiments of the present disclosure.

FIG. 2A illustrates an example of one type of radiotherapy device 130 (e.g., Leksell Gamma Knife), according to some embodiments of the present disclosure. As shown in FIG. 2A, in a radiotherapy treatment session, a patient 202 may wear a coordinate frame 220 to keep stable the patient's body part (e.g., the head) undergoing surgery or radiotherapy. Coordinate frame 220 and a patient positioning system 222 may establish a spatial coordinate system, which may be used while imaging a patient or during radiation surgery. Radiotherapy device 130 may include a protective housing 214 to enclose a plurality of radiation sources 212. Radiation sources 212 may generate a plurality of radiation beams (e.g., beamlets) through beam channels 216. The plurality of radiation beams may be configured to focus on an isocenter 218 from different directions. While each individual radiation beam may have a relatively low intensity, isocenter 218 may receive a relatively high level of radiation when multiple doses from different radiation beams accumulate at isocenter 218. In certain embodiments, isocenter 218 may correspond to a target under surgery or treatment, such as a tumor.

Figure 2B:
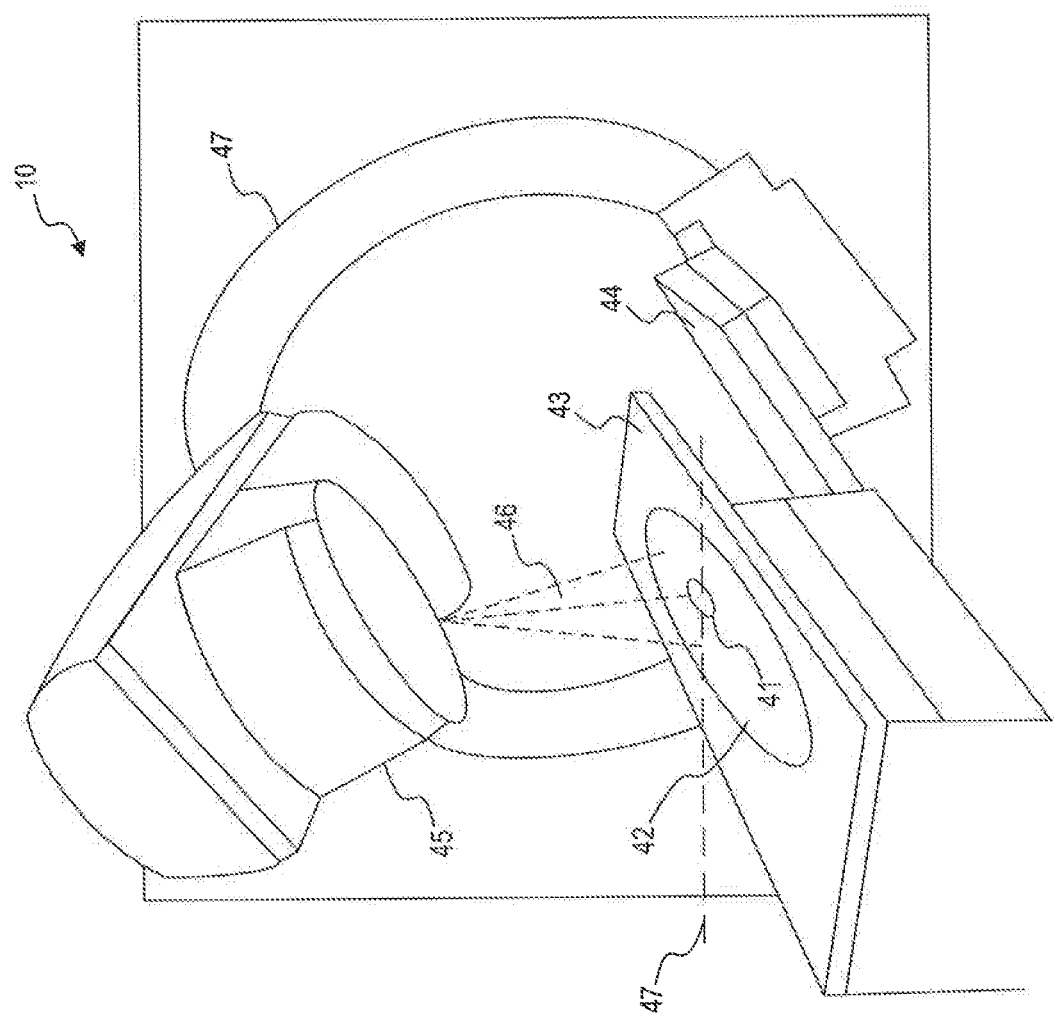
FIG. 2B illustrates another radiotherapy device, a linear accelerator, according to some embodiments of the present disclosure.

FIG. 2B illustrates another example of a radiotherapy device 130 (e.g., a linear accelerator 10), according to some embodiments of the present disclosure. Using a linear accelerator 10, a patient 42 may be positioned on a patient table 43 to receive the radiation dose determined by the treatment plan. Linear accelerator 10 may include a radiation head 45 that generates a radiation beam 46. The entire radiation head 45 may be rotatable around a horizontal axis 47. In addition, below the patient table 43 there may be provided a flat panel scintillator detector 44, which may rotate synchronously with radiation head 45 around an isocenter 41. The intersection of the axis 47 with the center of the beam 46, produced by the radiation head 45, is usually referred to as the "isocenter". The patient table 43 may be motorized so that the patient 42 can be positioned with the tumor site at or close to the isocenter 41. The radiation head 45 may rotate about a gantry 47, to provide patient 42 with a plurality of varying dosages of radiation according to the treatment plan.

FIG. 2C illustrates an embodiment of data processing device 110 that is communicatively coupled to a database 120 and a hospital database 121. As shown in FIG. 2C, data processing device 110 may include a processor 250, a memory or storage device 260, and a communication interface 270. Memory/storage device 260 may store computer executable instructions, such as an operating system 262, training/prediction software 264, treatment planning software 265, and any other computer executable instructions to be executed by the processor 250.

Processor 250 may be communicatively coupled to a memory/storage device 260 and configured to execute the computer executable instructions stored thereon. For example, processor 250 may execute training/prediction software 264 to implement functionalities of training module 112 and/or prediction module 114. In addition, processor device 250 may execute treatment planning software 265 (e.g., such as Monaco® software manufactured by Elekta) that may interface with training/prediction software 264.

Processor 250 may communicate with database 120 through communication interface 270 to send/receive data to/from database 120. Database 120 may include one or both of training database 122 and testing database 124. One skilled in the art would appreciate that database 120 may include a plurality of devices located either in a central or distributed manner. In addition, processor 250 may communicate with the hospital database 121 to implement functionalities of oncology information system 144 as shown in FIG. 1.

Processor 250 may be a processing device, include one or more general-purpose processing devices such as a microprocessor, central processing unit (CPU), graphics processing unit (GPU), or the like. More particularly, processor device 250 may be a complex instruction set computing (CISC) microprocessor, reduced instruction set computing (RISC) microprocessor, very long instruction Word (VLIW) microprocessor, a processor implementing other instruction sets, or processors implementing a combination of instruction sets. Processor 250 may also be one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some embodiments, processor 250 may be a special-purpose processor, rather than a general-purpose processor.

Memory/storage device 260 may include a read-only memory (ROM), a flash memory, a random access memory (RAM), a static memory, etc. In some embodiments, memory/storage device 260 may include a machine-readable storage medium. While the machine-readable storage medium in an embodiment may be a single medium, the term "machine-readable storage medium" should be taken to include a single medium or multiple media (e.g., a centralized or distributed database, and/or associated caches and servers) that store the one or more sets of computer executable instructions or data. The term "machine-readable storage medium" shall also be taken to include any medium that is capable of storing or encoding a set of instructions for execution by the machine and that cause the machine to perform any one or more of the methodologies of the present disclosure. The term "machine readable storage medium"

shall accordingly be taken to include, but not be limited to, solid-state memories, optical and magnetic media.

Communication interface 270 may include a network adaptor, a cable connector, a serial connector, a USB connector, a parallel connector, a high-speed data transmission adaptor such as fiber, USB 3.0, thunderbolt, and the like, a wireless network adaptor such as a WIFI adaptor, a telecommunication (3G, 4G/LTE and the like) adaptor, and the like. The communication interface 270 may provide the functionality of a local area network (LAN), a wireless network, a cloud computing environment (e.g., software as a service, platform as a service, infrastructure as a service), a client-server, a wide area network (WAN), and the like. Processor 250 may communicate with database 120 or other devices or systems via communication interface 270.

In a radiotherapy treatment, generating the treatment plan may include the delineation of a target, such as a tumor. In some embodiments, the delineation of one or more OARs, healthy tissue surrounding the tumor or in close proximity to the tumor, may be required. Therefore, segmentation of the OAR may be performed when the OAR is close to the target tumor. In addition, if the tumor is close to the OAR (e.g., prostate in near proximity to the bladder and rectum), segmentation of the OAR may allow study of the dose distribution not only in the target, but also in the OAR.

Figure 3A:
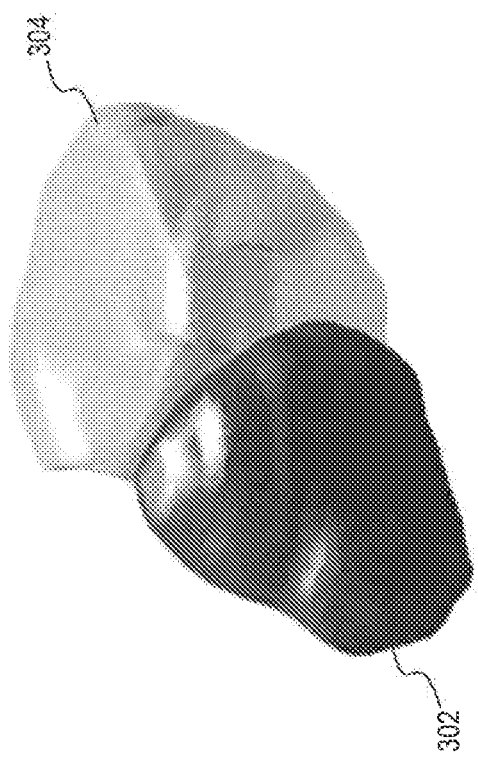
FIG. 3A illustrates a target tumor and an OAR, according to some embodiments of the present disclosure.

FIG. 3A illustrates a target 302 and an OAR 304, according to some embodiments of the present disclosure. It is noted that target 302 and OAR 304 shown in FIG. 3A represent a 3D reconstruction of segmented target and OAR. In order to delineate the target tumor 302 from the OAR 304, medical images, such as MRI images, CT images, PET images, fMRI images, X-ray images, ultrasound images, radiotherapy portal images, SPECT images and the like, of the patient undergoing radiotherapy may be obtained non-invasively by image acquisition device 140 to reveal the internal structure of a body part. Based on the information from the medical images, a 3D structure similar to the one shown in FIG. 3A may be obtained. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker) or automatically (e.g., using a program such as the Atlas-based Autosegmentation software, ABAS®, manufactured by Elekta). In certain embodiments, the 3D structure of a target tumor or an OAR may be generated automatically by prediction module 114.

After the target tumor and the OAR(s) have been delineated, a dosimetrist, physician or healthcare worker may determine a dose of radiation to be applied to the target tumor and any OAR proximate to the tumor (e.g., left and right parotid, optic nerves, eyes, lens, inner ears, spinal cord, brain stem, and the like). After the dose is determined for each anatomical structure (e.g., target tumor, OAR), a process known as inverse planning may be performed to determine one or more plan parameters, such as volume delineation (e.g., define target volumes, contour sensitive structures), margins around the target tumor and OARs, dose constraints (e.g., full dose to the tumor target and zero dose to any OAR; 95% of dose to PTV while spinal cord ≤45 Gy, brain stem ≤55 Gy, and optic structures <54 Gy), beam angle selection, collimator settings, and beam-on times. The result of inverse planning may constitute a radiation therapy treatment plan that may be stored in treatment planning system 142. Radiotherapy device 130 may then use the generated treatment plan having these parameters to deliver radiation therapy to a patient.

During a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Some of these parameters may be correlated. For example, tuning one parameter (e.g., weights for different objectives, such as increasing the dose to the target tumor) in an attempt to change the treatment plan may affect at least one other parameter, which in turn may result in the development of a different treatment plan.

The process of creating a treatment plan may be time consuming. In addition, different users (e.g., physicians, healthcare workers, dosimetrists, and the like) may prioritize parameters differently. For instance, different users may create different contours of the same target tumor or same OAR(s), use different dosage regimes for the various anatomies (e.g., tumor and OAR) and the like. Therefore, it may be difficult to arrive at a consensus on an objective standard to evaluate a particular treatment plan. Under such circumstances, effective use of information (e.g., training data) derived from previous treatments, such as statistical estimations of various parameters or relationships among these parameters, may improve the consistency, accuracy, and efficiency of generating treatment plans.

The predictive module 114 may be used in the case of automated treatment planning. In this case, predictive module 114 may determine an objective parameter such as dose-volume histograms (DVHs). The predicted DVHs may be used to develop a treatment plan for the actual treatment of the patient. Alternatively, prediction module 114 may predict a first DVH, and treatment planning system 142 may determine a second DVH. The predicted first DVH may be compared to the second DVH as part of a quality assurance process. Thus, in some embodiments, prediction module 114 may assess parameters, such as DVHs, as a safeguard to reduce the likelihood of formulating a treatment plan that results in high levels of radiation received by the OARs. If OARs receive too much radiation under an initial dose plan, the initial dose plan may be rejected or may need to be changed to meet a desired radiation level requirement.

A DVH typically illustrates the amount of a certain volume of a target (e.g., a tumor or an OAR) that is to be irradiated with a radiation dose equal to or higher than a predetermined specific radiation value. (See FIG. 3B, discussed below.) For example, given a specific set of voxels V in a target or organ (v is a voxel in V) and a dose D, DVH can be defined as follows:

$$DVH(D) = \frac{|v \in V : d(v) \geq D|}{|v|} \quad (1)$$

where d(v) is the actual dose in a certain voxel v and |.| denotes the total number of voxels in the volume V.

DVHs may also be interpreted from a probabilistic point of view. For example, if D denotes a specific dose and d denotes a random variable, then a cumulative distribution function can be defined as $F_D(D)=P(d \leq D)$, which is the probability that d is less than or equal to D. $P(d \leq D)$ can be calculated by integrating over the probability density function $p_D(d)$ as follows:

$$P(d \leq D) = \int_{-\infty}^{D} p_D(s)ds = \int_0^D p_D(s)ds \quad (2)$$

Further, because dose D, is always positive, the minimum must always be zero. By combining equations (1) and (2), DVHs can also be interpreted as follows:

$$DVH(D)=1-F_d(D)=1-\int_0^D p_D(s)ds \qquad (3)$$

Figure 3B:
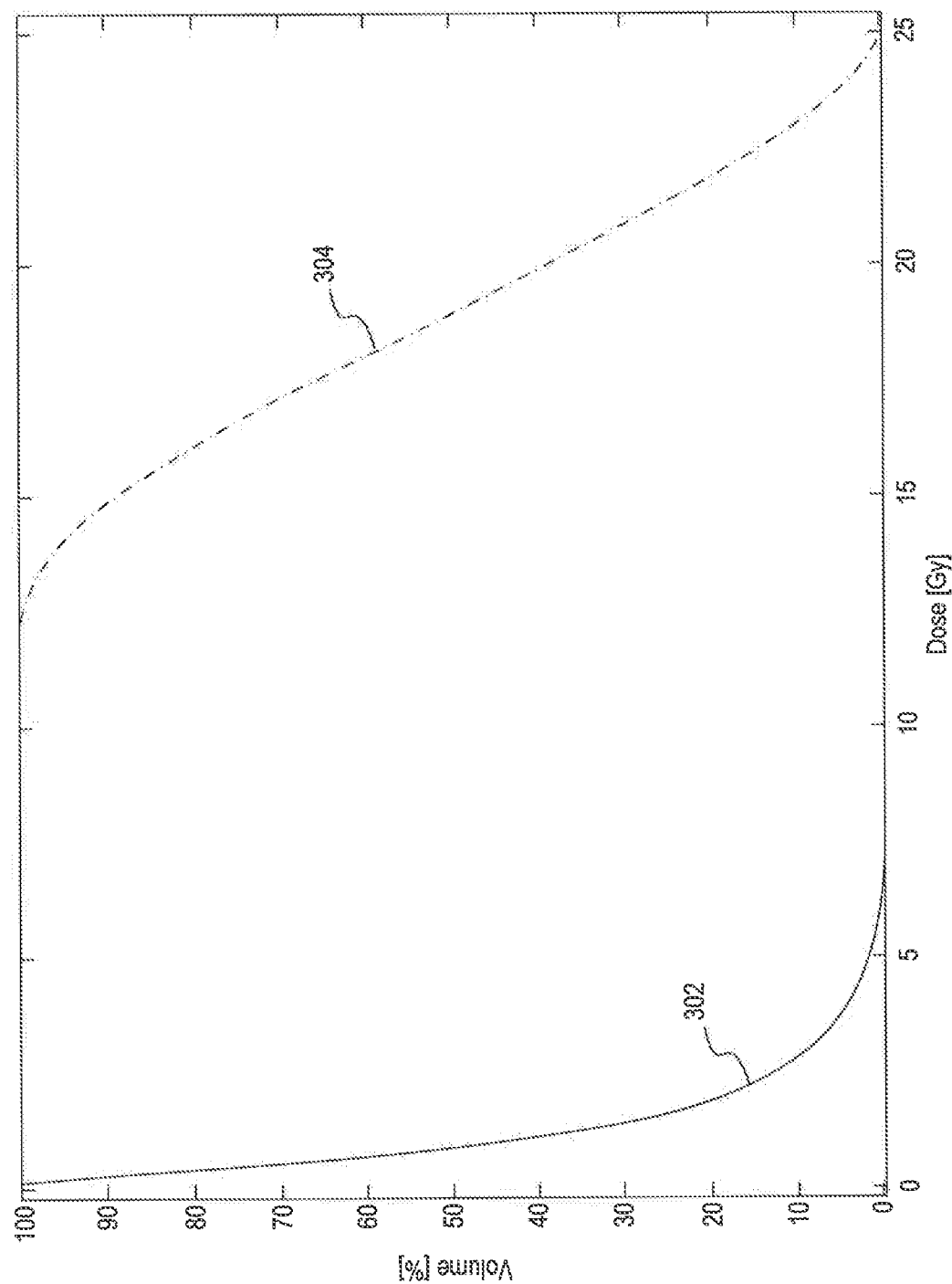
FIG. 3B illustrates an exemplary dose-volume histogram (DVH) for a target and an exemplary DVH for an OAR, according to some embodiments of the present disclosure.

As discussed above, DVHs may then be used to assess the dose for a region of interest located in different parts of the body relevant to the treatment. FIG. 3B illustrates an embodiment of two DVHs, for example, based on a treatment plan for a treating a target tumor and an OAR located adjacent the target tumor. A plurality of DVH curves may be provided depending on the region of interest (e.g., prostate, head and neck, brain, lung, heart, and the like) to be irradiated. As shown in FIG. 3B, curve 302 is a DVH for an OAR, where most of the volume (e.g., voxels) of the OAR receive less than a 5 Gy dose of radiation. Curve 304 is a DVH for a target tumor (e.g., PTV), where most of the volume of the target tumor receives more than a 15 Gy dose of radiation. During a treatment session, the target tumor will preferably receive a high and uniform dose of radiation, according to the treatment plan, while any surrounding healthy tissue (e.g., OAR), will preferably receive a radiation dose as small as possible.

As described above and in more detail below, the present disclosure provides a method of using information obtained from one or more previous treatment plans to improve the efficiency and effectiveness of new treatment planning processes. The method may be carried out by radiotherapy system 100. In some embodiments, the method may include a data training process, in which training module 112 accesses training database 122 to select data from prior treatment plans and then utilizes the training data to generate one or more predictive models. The method may also include a data prediction process, in which prediction module 114 utilizes testing data in conjunction with the one or more predictive models to predict one or more outcomes (e.g., output vectors and output elements). The predicted outcomes may then be used to develop a treatment plan.

In some embodiments, the training process and predictive process may be incorporated into a single process, in which data flow require co-operation of both processes. In some embodiments, the two processes may operate separately, for example, on separate machines and/or at different times, where the operation of one process does not necessarily require the co-operation of the other process. In such embodiments, data sharing between the two processes may use a database, or maybe performed in an off-line mode.

Data Training

Figure 4:
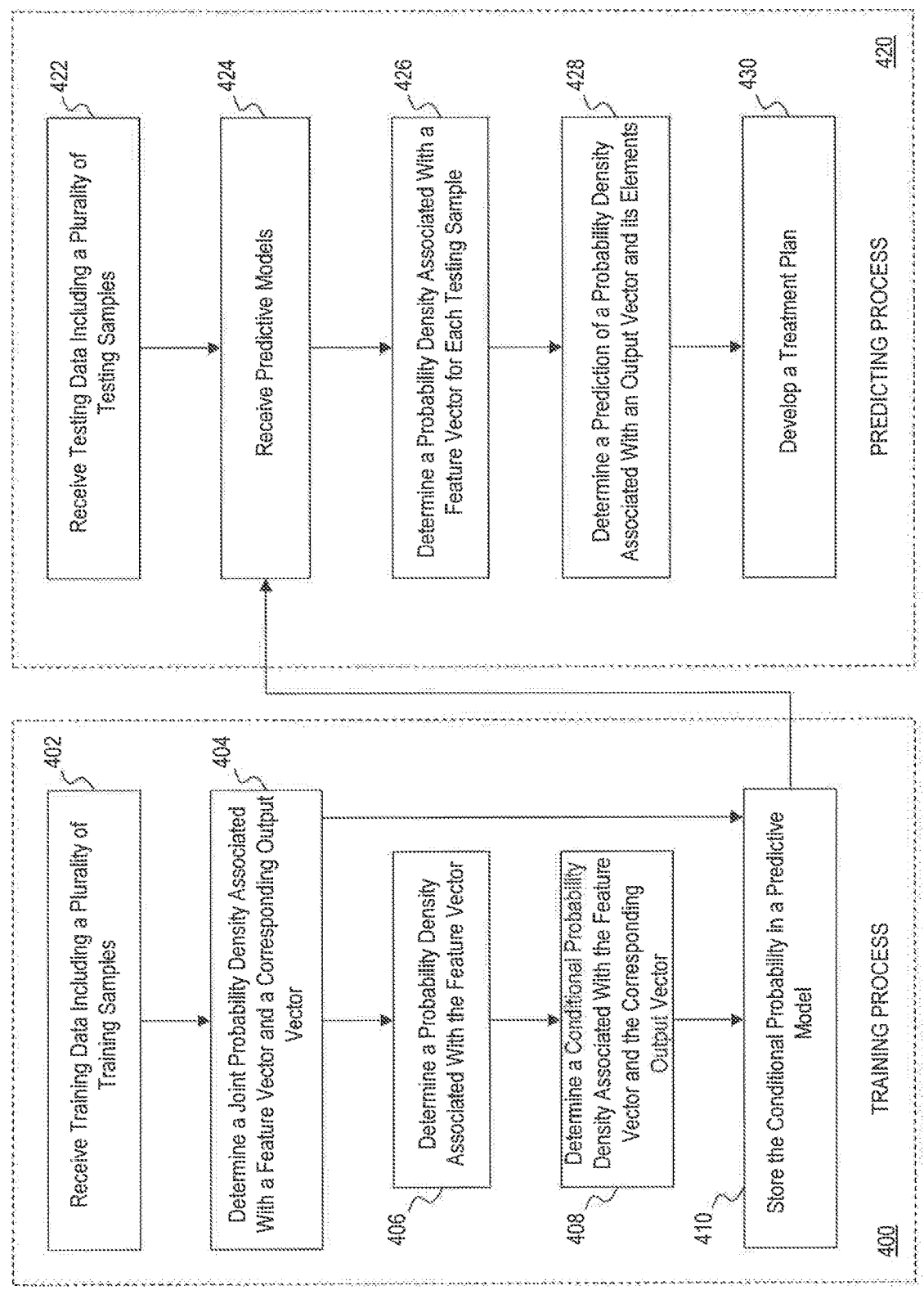
FIG. 4 is a flowchart illustrating an exemplary method of a data training process and a prediction process, according to some embodiments of the present disclosure.

FIG. 4 is a flowchart of a method of data training and data prediction, according to some embodiments of the present disclosure. FIG. 4 includes two processes: a data training process 400 and a data prediction process 420. As described above, data training process 400 and data prediction process 420 may be incorporated into a single process or may be separate processes. In some embodiments, data training process 400 may be implemented by training module 112. Similarly, data prediction process 420 may be implemented by prediction module 114.

Data training process 400 may include a step 402, in which training module 112 may receive training data from training database 122. The training data may include a plurality of previous treatment plans that are stored in training database 122. For example, the stored training data may include diagnostic images, treatment images (dose maps), segmentation information, and the like, associated with one or more previous treatment plans. The training data may include a plurality of training samples. Each training sample may comprise a feature vector and a corresponding output vector.

The feature vector may include one or more feature elements. Each feature element may indicate an observation of a medical image (e.g., provided by image acquisition device 140 or stored in training database 122) used in a past radiotherapy session. The observation may be a distance between a volume (e.g., a voxel) and an anatomical region, such as a target or the surface of the body part in the medical image. In another example, the observation may include spatial coordinates of an anatomical region or a probability that an anatomical region includes a particular tissue type. In another example, the feature element may include patient specific information, responsible physician, organ or volume of interest segmentation data, functional organ modeling data (e.g., serial versus parallel organs, and appropriate dose response models), radiation dosage (e.g., also including dose-volume histogram (DVH) information), lab data (e.g., hemoglobin, platelets, cholesterol, triglycerides, creatinine, sodium, glucose, calcium, weight), vital signs (blood pressure, temperature, respiratory rate and the like), genomic data (e.g., genetic profiling), demographics (age, sex), other diseases affecting the patient (e.g., cardiovascular or respiratory disease, diabetes, radiation hypersensitivity syndromes and the like), medications and drug reactions, diet and lifestyle (e.g., smoking or non-smoking), environmental risk factors, tumor characteristics (histological type, tumor grade, hormone and other receptor status, tumor size, vascularity cell type, cancer staging, gleason score), previous treatments (e.g., surgeries, radiation, chemotherapy, hormone therapy), lymph node and distant metastases status, genetic/protein biomarkers (e.g., such as MYC, GADD45A, PPM1D, BBC3, CDKN1A, PLK3, XPC, AKT1, RELA, BCL2L1, PTEN, CDK1, XIAP, and the like), single nucleotide polymorphisms (SNP) analysis (e.g., XRCC1, XRCC3, APEX1, MDM2, TNFR, MTHFR, MTRR, VEGF, TGFβ, TNFα), and the like. The feature vector may include one or more such feature elements, regardless of whether these feature elements are related to each other or not.

The output vector may include one or more output elements. Each output element may indicate a corresponding plan outcome or parameter in the past radiotherapy session based on the observation(s) included in the feature vector. For example, the output element may include the dose applied or received at a particular spatial location (e.g., a voxel). In another example, the output element may include a patient survival time based on observations such as a treatment type, treatment parameters, patient history, and/or patient anatomy. Additional examples of output elements include, but not limited to, a normal tissue complication probability (NTCP), a region displacement probability during treatment, or a probability that a set of coordinates in a reference image is mapped to another set of coordinates in a target image. The output vector may include one or more such output elements, regardless of whether these output elements are related to each other or not.

As an example of an embodiment, an output element may include a dose to be applied to a voxel of a particular OAR. Further, a feature element may be used to determine the output element. The feature element may include a distance between the voxel in the OAR and the closest boundary voxel in a target tumor. Therefore, the feature element may include a signed distance x indicating the distance between a voxel in an OAR and the closest boundary voxel in a target for the radiation therapy. The output element may include a dose D in the voxel of the OAR from which x is measured.

In some other embodiments, each training sample may correspond to a particular voxel in the target or OAR, such that multiple training samples within the training data corresponding to the whole volume of the target or OAR and other anatomical portions subject to the radiotherapy treatment.

At step 404, training module 112 may determine a joint probability density associated with a feature vector and a corresponding output vector based on the training data. The joint probability density may indicate a likelihood that both an observation indicated by the feature vector and a plan outcome indicated by the corresponding output vector are present in the training data.

For example, the feature vector may include a single element, such as assigned distance x, and the corresponding output vector may include a single output element, such as the dose D. Training module 112 may determine a joint probability density p(x, D) using a density estimation method such as a Kernel Density Estimation (KDE) algorithm. KDE is a non-parametric algorithm that applies a kernel function to each data point and then sums the kernels. A kernel may be defined as a function satisfying the following properties:

$$\int \kappa(x)dx = 1, \int x\kappa(x)dx = 0, \int x^2 \kappa(x)dx > 0.$$

Specifically, KDE is used to make an estimate $f'(x)$ of a density function $f(x)$ for some parameter x given N observations $x_i$ and a kernel $\kappa_h(x)$. An univariate KDE (e.g., one dimensional KDE) can be written as follows:

$$f'(x) = \frac{1}{N} \sum_{i=1}^{N} \kappa_h(x - x_i) \quad (6)$$

where h denotes the bandwidth parameter and $$\kappa_h(x) = \frac{1}{h}\kappa\left(\frac{x}{h}\right).$$

A KDE of a joint probability distribution $f'(x)$, where $x=(x_1, x_2)^T$ is generally defined as:

$$f'(x) = \frac{1}{N} \sum_{i=1}^{N} \kappa_H(x - x_i) \quad (7)$$

where the ith observation $x_i = (x_{1i}, x_{2i})^T$ and $$\kappa_H(x-x_i) = \det(H)^{-1/2} \kappa(H^{-1/2}(x-x_i)) \quad (8)$$

$$H = \begin{pmatrix} h_1^2 & h_{12} \\ h_{12} & h_2^2 \end{pmatrix}$$

is a symmetric and positive-definite matrix.

In some embodiments, H may be simplified to a diagonal matrix. Then the KDE can be expressed as $$f'(x) = \frac{1}{N} \sum_{i=1}^{N} \kappa_h(x_1 - x_{1i})\kappa_h(x_2 - x_{2i}) \quad (9)$$

where $h = \sqrt{h_1 h_2}$ and $h_1^2$ and $h_2^2$ can be identified as the diagonal elements in H. Thus, training module 112 may use the KDE algorithm to determine a joint probability density p(x, D) when the feature element includes the signed distance x and the corresponding output element includes the dose D.

In some embodiments of training process 400, step 406 and step 408, described below, may be optional. Therefore, in one embodiment, training process 400 may include steps 402, 404, and 410. In another embodiment, training process may include steps 402, 404, 406, 408, and 410.

At step 406, training module 112 may determine a probability density associated with the feature vector, or each element within the feature vector, based on the training data. The probability density may indicate a likelihood that the observation indicated by the feature vector, or each element (e.g., the signed distance x) within the feature vector, is present in the training data. For example, when the feature vector includes the signed distance x, training module 112 may determine the probability density p(x) for the entire training data using a one-dimensional KDE algorithm, as described above.

At step 408, training module 112 may determine a conditional probability density (e.g., P(y|x)) associated with a feature vector (e.g., vector x) and the corresponding output vector (e.g., vector y) based on the determined joint probability (e.g., P(y,x)=P(y|x)p(x)) and the determined probability density (e.g., P(x)) associated with the feature vector x. In some embodiments, feature vector x may correspond to a distance, a spatial coordinate, patient specific information, and the like. In some embodiments, output vector y may correspond to a dose, a tumor control probability, a normal tissue complication probability, a patient survival time, a region displacement probability during treatment, and the like.

A feature vector may include a plurality of feature elements (e.g., x=[x1, x2, x3, . . . ]), and an output vector may contain a plurality of output elements (e.g., y=[y1, y2, y3, . . . ]). In one embodiment, training module 112 may determine a joint probability distribution based on all the feature elements and all the output elements. In another embodiment, training module 112 may determine a joint probability distribution based on all the feature elements and each output element.

The conditional probability density may indicate a likelihood that the plan outcome indicated by the corresponding output vector or element (e.g., the dose D) is present in the training data given a presence of the feature vector or element (e.g., the signed distance x) in the training data. For example, when the feature vector includes the signed distance x and the corresponding output vector includes the dose D, training module 112 may determine the conditional probability density of the dose D given a distance x as follows:

$$p(D|x) = \frac{p(x, D)}{p(x)} \quad (10)$$

As described above, using a distance x to determine a probability density of a dose D, is one embodiment where both the input and the output are single scalar variables. In other embodiments, a model may be created to use multiple variables for x, (such as a plurality of distance coordinates to an OAR, a plurality of distance coordinates to a tumor, spatial coordinates, tissue probabilities, information from original images, information from post-processed images) to estimate the probability density for a particular variable y (e.g., determine the probability density of a dose or determine a probability density of a tumor control probability and the like). Therefore, in an embodiment, a probability density of a tumor control probability based on multiple tissue probabilities may be determined (e.g., $P(y|x_1, x_2, x3, \ldots)$).

The training of the one or more predictive models may be performed either offline or online. For example, the joint probability may be estimated and stored before beginning the treatment process (e.g., offline) or the joint probability may be estimated in real-time during the treatment process (e.g., online). In another embodiment, treatment plans that differ significantly from prior treatment plans can be detected. In this case, the training process may be conducted offline.

In an embodiment, the training process may or may not use data from other patients. In some embodiments, training data may be used to adapt the treatment plan for the patient by comparing a plurality of previous treatment plans developed for the same patient. In another embodiment, training data may include treatment plans from a plurality of other patients with the same or similar medical diagnosis.

Generate Predictive Model

At step 410, training module 112 may store the conditional probability (e.g., $P(y|x)$), which may constitute the result of training process 400, in training database 122. For example, training module 112 may store one or more conditional probabilities (e.g., $p(D|x)$, where D is dose) in training database 122 as a predictive model. In an embodiment, training module 112 may store one or more joint probabilities (e.g., $p(y,x)$) in training database 122 as a predictive model. Thus, the predictive model may be determined by using either the one or more joint probabilities or the one or more conditional probabilities.

As described above, this predictive model may indicate information obtained or derived from one or more past radiotherapy sessions. For example, the predictive model may include statistical estimations of parameters used in the past radiotherapy sessions. The predictive model may also include statistical estimations of relationships among parameters used in the past radiotherapy sessions. The predictive model may also include statistical estimations of outcomes of the past radiotherapy sessions.

Apply Predictive Model(s) to Testing Data

Once the predictive models are obtained, they can be used in prediction process 420 to predict the probability density associated with the output vector, or an output element, for the development of a new treatment plan.

At step 422, prediction module 114 may receive testing data including a plurality of testing samples. In some embodiments, testing data and testing samples may be similar to training data and training samples described above. Each testing sample may include a feature vector, which may include one or more feature elements, Each testing sample may include an output vector, which may include one or more output elements. For example, while training data and training samples may relate to previous or past treatments, testing data may relate to a new patient, or a new treatment session of the same patient. For instance, the observation of a medical image used in a past treatment session may form part of the feature vector in the training data. On the other hand, observation of a medical image used in the new treatment session may form part of the feature vector in the testing data. In other words, while the formats of the training data and the testing data may be similar, training data may relate to past treatments and testing data may relate to the new treatment.

At step 424, prediction module 114 may receive one or more predictive models from training module 112. Testing data may be used in conjunction with the one or more predictive models to predict objective parameters of one or more outcomes. To predict the objective parameters (e.g., feature vectors, feature elements, output vectors, and output elements), testing data may be applied to the one or more predictive models. The predicted outcomes may then be used to develop a treatment plan.

For example, when the feature vector includes the signed distance x and the corresponding output vector includes the dose D, the conditional probability density may be $p(D|x)$ as determined at step 408 and stored at step 410. Alternatively, when the feature vector includes spatial coordinates and tissue probabilities, the corresponding output vector may be a region displacement probability during treatment (e.g., $p(r_x, r_y, r_z | x, y, z, t)$, where $(r_x, r_y, r_z)$ is the region displacement vector given spatial coordinates (x,y,z) and a tissue probability t).

At step 426, prediction module 114 may determine a probability density associated with the feature vector of each testing sample based on the testing data. The probability density may indicate a likelihood that an observation indicated by the feature vector is present in the testing data. For example, when the feature vector includes the signed distance x, prediction module 114 may estimate the probability density $p^*(x)$ for the new plan. In an embodiment, the feature vector may be treated as a sequence of Dirac pulses, denoted as $\delta(x)$, in order to estimate the probability density $p(x^*)$:

$$p(x^*) = \frac{1}{|S|} \sum_{s \in S} \delta(x - X_s^*) \tag{13}$$

where |S| denotes the number of elements in S.

In some embodiments, the feature vector may include arbitrary dimension and/or multiple types of data (e.g., continuous, ordinal, discrete, and the like). In some embodiments, images used in the training process and predicting processes may include diagnostic images, treatment images (dose maps), and/or segmentation images. In some embodiments, the feature vector may include a distance to predetermined anatomical regions, such as the target or the OAR(s) or the patient surface. Such information may be summarized using an Overlap-Volume Histogram. Distances to multiple regions of interest may also be included in the feature vector. In some embodiments, the feature vector may include global information, such as spatial coordinates and/or tissue probabilities. In some embodiments, the feature vector may include features derived from a convolution of images with at least one linear filter (e.g., local phase, gradients, edge, or corner detectors). In some embodiments, the feature vector may include features derived by a transformation of one or more images (e.g., Fourier transform, Hilbert transform, Radon transform, distance transform, discrete cosine transform, wavelet transform). In each of these embodiments described above regarding the feature vector, a corresponding transformation to the output probability density may be applied.

In some embodiments, the feature vector may include information based on "information theoretical measures" (e.g., mutual information, normalized mutual information, entropy, Kullback-Leibler distance, and the like). In some embodiments, the feature vector may include a feature descriptor providing a higher-dimensional representation as utilized in the field of computer vision, such feature descriptor may include characteristics of a particular voxel of the image, such as SIFT (Scale-invariant feature transform), SURF (Speeded Up Robust Features), GLOH (Gradient Location and Orientation Histogram), or HOG (Histogram of Oriented Gradients). In another embodiment, the covariance/correlation between a plurality of image regions (e.g., two or more voxels) can be captured using a higher-dimensional representation. In some embodiments, the feature vector may include, for example, patient information such as age, gender, tumor size, a responsible physician and the like.

At step 428, prediction module 114 may determine a prediction of a probability density associated with an output vector, or its elements, based on the probability densities determined for the plurality of testing samples and the one or more predictive models. Specifically, the output vector can be used to detect one or more important features for a favorable outcome. The prediction of the probability density may indicate a likelihood of a plan outcome indicated by the output vector or its element(s) to be made in the new treatment plan.

In some embodiments, the output vector may include probability distribution of arbitrary dimensions; the dose; the tumor control probability (TCP) or normal tissue complication probability (NTCP), either on a micro- or macroscale; or patient survival time based on, for example, treatment type, treatment parameters, patient history, or anatomy.

In some embodiments, the determination of the prediction of the probability density associated with the output vector may be carried out in a spatial domain. In some embodiments, this process may be performed in the frequency domain (e.g., Fourier domain, native to MRI acquisition). In some embodiments, the process may be performed in Radon transform space, for example, native to CT acquisition. In some embodiments, the prediction may be used on compressed images that use, for example, wavelet transforms, and the process may be performed in wavelet transform space.

The predicted probability distribution may be used to derive point-estimates and corresponding measures of variation, expressed, for example, as the moments of the probability distribution. In one embodiment, an estimated spatial dose map may be computed by taking the mean (i.e., first moment) of the distribution. In another embodiment, the spatial dose variability may be represented by the standard deviation (i.e., square root of the central second moment).

In some embodiments, the output vector may be used to predict the probability density of various characteristics. For instance, the output vector may include the probability that the anatomical region of interest may move during treatment, such as the lungs, heart, or prostate. In some embodiments, the output vector (e.g., a 3D vector) may be used to guide deformable registration by modeling correlations of a patient's anatomy, for example, the output vector may include the probability that a set of coordinates in an atlas image is mapped to another set of coordinates in a target image, or vice versa. In some embodiments, the output vector may be sampled by Monte Carlo simulations of radiation transport and used to speed up calculations in subsequent dose calculations. In some embodiments, the predicted probability density may be used to detect outliers in commissioning of radiotherapy systems.

The prediction process 420 may allow for the development of a treatment plan, at step 430, by utilizing a plurality of objective parameters of one or more outcomes. For example, prediction module 114 may determine a dose-volume histogram (DVH) based on the determined prediction of the probability density associated with the output element. In this case, the feature vector includes the signed distance x and the corresponding output vector includes the dose D. The prediction of the probability density p*(D) may be determined as follows:

$$p^*(D) = \int p(D|x) p^*(x) dx \quad (11)$$

and the corresponding DVH(D) may be calculated as follows:

$$\mathrm{DVH}(D) = 1 - \int_0^D p^*(s) ds \quad (12).$$

In an embodiment, at step 430, the prediction process 420 may allow for the validation of a treatment plan, e.g., for the purposes of quality assurance or training. For example, step 430 may allow for the validation of one or more previously generated treatment plans with the newly generated treatment plan.

Figure 5:
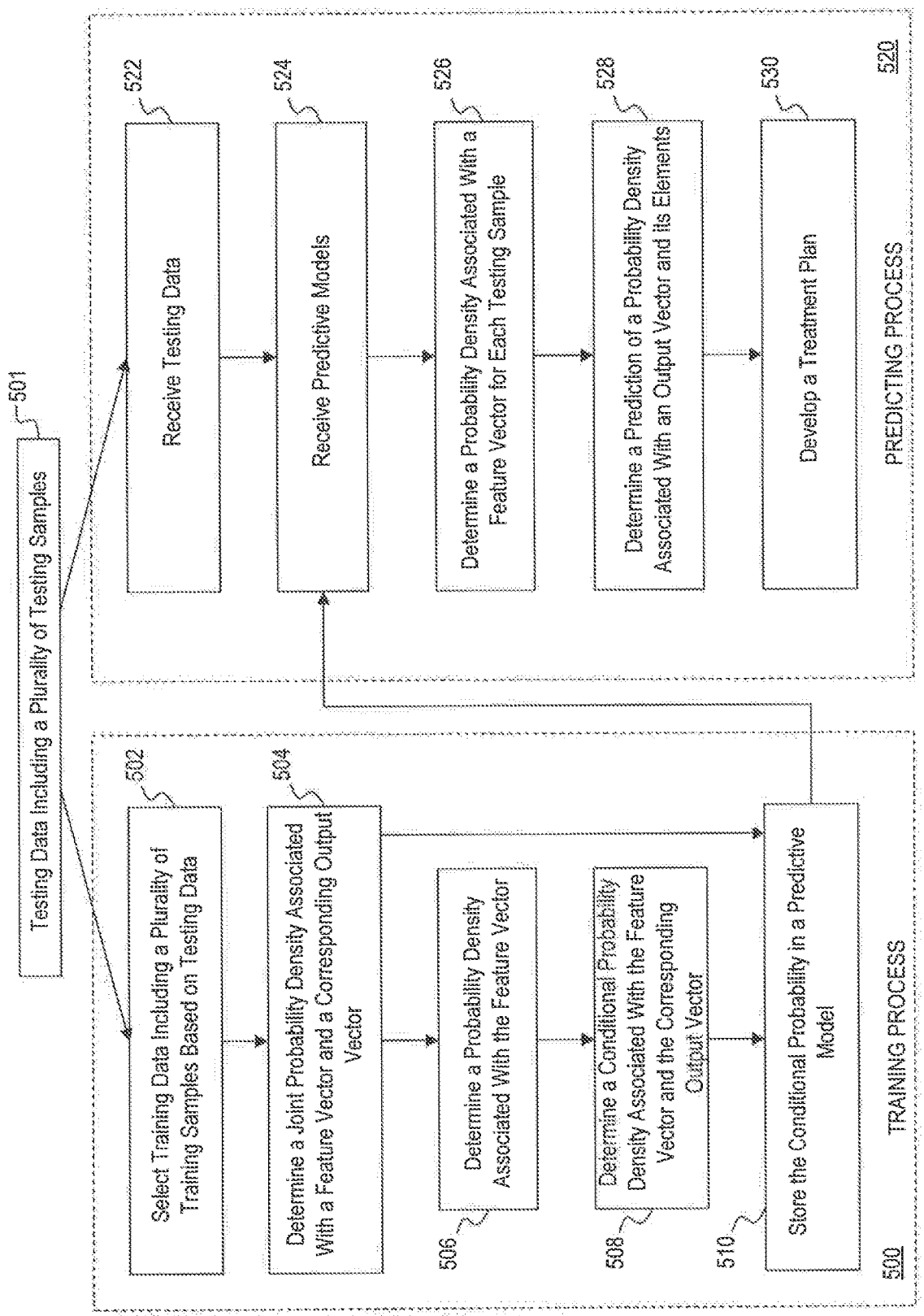
FIG. 5 is a flowchart illustrating an exemplary method of utilizing patient specific testing data, according to some embodiments of the present disclosure.

FIG. 5 is a flowchart of another embodiment that utilizes patient specific testing data to select training data to perform a training process 500 and a data prediction process 520. In some embodiments, processes 500 and 520 may be similar to processes 400 and 420 as previously described with respect to FIG. 4, respectively, with some differences that will be described below. Referring to FIG. 5, testing data 501 may be used in training process 500 and prediction process 520. In some embodiments, testing data 501 may include a plurality of testing samples. In some embodiments, testing data 501 and its testing samples may be similar to the testing data received at step 424 in FIG. 4. As noted above, FIG. 5 may be similar to FIG. 4. The differences between FIG. 4 and FIG. 5 include the way patient specific testing data (e.g., testing data 501) are utilized. For example, referring to FIG. 5, training process 500 may utilize patient specific testing data 501 to generate one or more predictive models. In some embodiments, patient specific testing data 501 may be used at step 502, where training module 110 may select a subset of training data from training database 122 based on testing data 501.

At step 504, training module 112 may determine a joint probability density associated with a feature vector and a corresponding output vector based on the training data selected at step 502. Step 504 may be similar to step 404 except the training data used in step 504 may be selected based on testing data 501.

In some embodiments of training process 500, step 506 and step 508, described below, may be omitted. Therefore, in one embodiment, training process 500 may include steps 502, 504, and 510. In another embodiment, training process may include steps 502, 504, 506, 508, and 510.

At step 506, probability density associated with a feature vector may be determined, similar to step 406. At step 508, a conditional probability associated with an output vector given a feature vector may be determined, similar to step 408.

At step 510, training module 112 may store one or more conditional probabilities in training database 122 as a predictive model. In some embodiments, training module 112 may store one or more joint probabilities in training database 122 as a predictive model. Thus, the predictive model may be determined based on either the one or more joint probabilities or the one or more conditional probabilities.

Once the predictive model(s) specific for a particular patient are generated by training module 112 (e.g., through training process 500), testing data 501 may be further used by prediction module 114 in conjunction with the one or more predictive models to predict one or more outcomes (e.g., output vectors or output elements).

For example, at step 522, testing data 501 may be received and used in prediction process 520 along with the one or more predictive models received from training module 112 (e.g., received at step 524).

At step 526, prediction module 114 may determine a probability density associated with the feature vector of each testing sample based on the testing data, similar to step 426.

At step 528, prediction module 114 may determine a prediction of a probability density associate with the output vector, or its elements, based on the probability densities determined for the plurality of testing samples and the one or more predictive models, similar to step 428.

Once the predicted outcomes are generated, the predicted outcomes may then be used either to develop a treatment plan or to validate a previously generated treatment plan, at step 530.

In some embodiments, a plurality of testing data may be received from treatment planning system 142, either in an online mode or an offline mode.

In addition to the KDE method described above, other density estimation methods may also be used to determine the joint probability density associated with a training sample or the probability density associated with the feature vector of a testing sample. Examples of density estimation methods include, but not limited to:

Non-parametric methods—non-parametric methods may estimate the density with minimum assumptions. Examples include the KDE described above, and artificial neural networks, which model the unknown function as a weighted sum of several sigmoids, each of which is a function of all the relevant explanatory variables.

Parametric methods—parametric methods assume a parameterized probability distribution and fit it to the data. An example is the Gaussian mixture model.

Monte Carlo based methods—this type of methods uses repeated random sampling to estimate a probability distribution and can therefore be used in limited instances such as simulations.

Machine learning methods—machine learning method can be extended to perform density estimation. Examples include transductive support vector machines (SVM), decision forests, random forests, regression models, and density estimation trees. Some of the density estimation methods may be particularly suitable for outlier detection or relevance determination, such as density estimation trees. Monte Carlo based methods and some machine learning methods, such as density estimation trees, may be better equipped to handle high-dimensional data.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present invention also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

Embodiments of the invention may be implemented with computer-executable instructions. The computer-executable instructions may be organized into one or more computer-executable components or modules. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described herein.

When introducing elements of aspects of the invention or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

What is claimed is:

1. A radiotherapy system for treating a target patient according to a treatment plan, the system configured to use training data associated with past treatment plans used to treat sample patients, the training data including a plurality of observations associated with conditions of the sample patients and derived from medical image data associated with the sample patients, the training data further including one or more plan outcomes reflecting outcomes resulting from the past treatment plans, or plan parameters reflecting design parameters of the past treatment plans, the system comprising:
  a processing device configured to generate the treatment plan, the processing device configured to execute instructions stored on a computer-readable medium that, upon execution, cause the processing device to perform operations including:
    determining a joint probability density indicating a likelihood that both at least one particular observation and at least one particular plan outcome of the one or more plan outcomes or plan parameter of the plan parameters are present in the training data;
    calculating a conditional probability based upon the determined joint probability density, wherein the conditional probability indicates a likelihood that the at least one particular plan outcome or the plan parameter is present in the training data;
    predicting a probability of a patient specific plan outcome or patient specific plan parameter based on the conditional probability and at least one patient specific observation associated with the target patient and derived from medical image data associated with the target patient;
    generating the treatment plan based on the prediction; and
    controlling a radiotherapy device to perform radiotherapy treatment according to the generated treatment plan.

2. The radiotherapy system of claim 1, wherein the training data comprise a plurality of training samples.

3. The radiotherapy system of claim 1, wherein the training data comprise a plurality of images.

4. The radiotherapy system of claim 3, wherein the training data comprise a training sample and the training sample includes characteristics of a voxel in an image.

5. The radiotherapy system of claim 3, wherein the plurality of images comprise at least one of a Magnetic Resonance Imaging (MRS) image, a 3D MRI image, a 2D streaming MRI image, a 4D volumetric MRI image, a Computed Tomography (CT) image, a Cone-Beam CT image; a Positron Emission Tomography (PET) image, a functional MRI (fMRI) image, an X-ray image, a fluoroscopic image, an ultrasound image, a radiotherapy portal image, or a single-photo emission computed tomography (SPECT) image.

6. The radiotherapy system of claim 1, wherein the past treatment plans are from a current patient, a plurality of other patients, or a combination thereof.

7. The radiotherapy system of claim 1, wherein the past treatment plans are from at least one of a single patient or a plurality of patients.

8. The radiotherapy system of claim 1, wherein the instructions additionally cause the processing device to calculate a probability that the particular observation is present in the training data; and
  wherein the conditional probability indicates a likelihood that the at least one particular plan outcome or the plan parameter is present in the training data given the probability that the at least one particular observation is present in the training data.

9. The radiotherapy system of claim 1, wherein determining the joint probability density or calculating the conditional probability comprises using at least one of a non-parametric method, a parametric method, a Monte Carlo based method, a regression method, a machine learning method, or combinations thereof.

10. A method for treating a target patient according to a treatment plan acid for use with training data associated with past treatment plans used to treat sample patients, the training data including a plurality of observations associated with conditions of the sample patients and derived from medical image data associated with the sample patients, the training data further including one or more plan outcomes reflecting outcomes resulting from the past treatment plans, or plan parameters reflecting design parameters of the past treatment plans, the method comprising:
  determining a joint probability density indicating a likelihood that both at least one particular observation and at least one particular plan outcome or plan parameter are present in the training data;
  calculating a conditional probability based upon the determined joint probability density, wherein the conditional probability indicates a likelihood that the at least one particular plan outcome or the plan parameter is present in the training data;
  predicting a probability of a patient specific plan outcome or plan parameter based on the conditional probability and at least one patient specific observation associated with the target patient and derived from medical image data associated with the target patient;
  generating the treatment plan based on the prediction; and
  controlling a radiotherapy device to perform radiotherapy treatment according to the generated treatment plan.

11. The method of claim 10, wherein determining the joint probability density comprises using at least one of a non-parametric method, a parametric method, a Monte Carlo based method, a regression method, a machine learning method, or combinations thereof.

12. The method of claim 10, wherein determining the conditional probability comprises using at least one of a non-parametric method, a parametric method, a Monte Carlo based method, a regression method, a machine learning method, or combinations thereof.

13. The method of claim 10, further comprising:
  receiving patient specific testing data, the patient specific testing data including at least one of imaging data, organ or volume of interest segmentation data, functional organ modeling data, radiation dosage, laboratory data, genomic data, demographics, other diseases affecting the patient, medications and drug reactions, diet and lifestyle, environmental risk factors, tumor characteristics, genetic/protein biomarkers, or previous medical treatments of the patient.

14. The method of claim 10, further comprising:
  receiving patient specific testing data associated with the target patient, the patient specific testing data including a patient specific feature vector, wherein the patient specific feature vector includes the at least one patient specific observation associated with the target patient.

15. The method of claim 10, further comprising:
  receiving patient specific testing data associated with the target patient, the patient specific testing data including a patient specific feature vector,
  wherein the patient specific feature vector includes the at least one patient specific observation associated with the target patient, wherein the feature vector comprises at least one of a distance to an anatomical region of interest, a tissue probability, a plurality of spatial coordinates, information derived from a convolution of images with at least one linear filter, information derived from a convolution of images with at least one non-linear filter, information derived from a transformation of one or more images, information based on theoretical measures, a feature descriptor of a type used in computer vision, a tumor size, a tumor type, a tumor location, a patient's age, a patient's gender, a patient's ethnicity, a patient's body-weight-index (BMI), patient information, or information of a responsible physician.

16. The method of claim 10, wherein the training data associated with past treatment plans includes a plurality of training samples, each of the training samples including a feature vector and an output vector corresponding to the feature vector.

17. The method of claim 16, wherein the output vector comprises at least one of a dose, a tumor control probability (TCP), a normal tissue complication probability (MVP), a patient survival time, a region displacement probability during treatment, or a probability that a set of coordinates in a reference image is mapped to another set of coordinates in a target image.

18. The method of claim 10, wherein the past treatment plans are from a current patient, a plurality of other patients, or a combination thereof.

19. The method of claim 10, comprising:
selecting the training data from a subset of all available training data based on patient specific testing data.

20. The method of claim 10, wherein the past treatment plans are from a single patient.

21. The method of claim 10, wherein the past treatment plans are from a plurality of patients.

22. The method of claim 10, further comprising:
receiving the training data, the training data including a plurality of training samples, each of the training samples including a feature vector and an output vector corresponding to the feature vector, wherein:

the feature vector includes one or more observations associated with conditions of the sample patients, wherein the one or more observations are derived from the medical image data associated with the sample patients; and the output vector includes the one or more plan outcomes or the plan parameters.

* * * * *

UNITED STATES PATENT AND TRADEMARK OFFICE
CERTIFICATE OF CORRECTION

| | | |
|---|---|---|
| PATENT NO. | : 10,765,888 B2 | Page 1 of 1 |
| APPLICATION NO. | : 16/029147 | |
| DATED | : September 8, 2020 | |
| INVENTOR(S) | : Sjolund et al. | |

It is certified that error appears in the above-identified patent and that said Letters Patent is hereby corrected as shown below:

In the Claims

In Column 21, Line 44, in Claim 5, delete "image;" and insert --image,-- therefor In Column 22, Line 4, in Claim 10, delete "acid" and insert --and-- therefor In Column 23, Line 15, in Claim 17, delete "(MVP)," and insert --(NTCP),-- therefor Signed and Sealed this
Sixteenth Day of February, 2021

Drew Hirshfeld
*Performing the Functions and Duties of the*
*Under Secretary of Commerce for Intellectual Property and*
*Director of the United States Patent and Trademark Office*